United States Patent [19]

Hartigan, Jr.

[11] Patent Number: 5,681,322
[45] Date of Patent: Oct. 28, 1997

[54] GAS STERILIZABLE INTRALUMINAL DELIVERY SYSTEM

[75] Inventor: James M. Hartigan, Jr., Wanaque, N.J.

[73] Assignee: Meadox Medicals, Inc., Oakland, N.J.

[21] Appl. No.: 339,492

[22] Filed: Nov. 14, 1994

[51] Int. Cl.[6] ............................................. A61F 11/00
[52] U.S. Cl. ............................ 606/108; 604/93; 604/264
[58] Field of Search ..................................... 606/108, 195,
606/198, 139, 1; 623/1, 900; 128/842, 843;
604/93, 102, 160, 164, 166, 902, 264

[56] References Cited

U.S. PATENT DOCUMENTS

| | | |
|---|---|---|
| 4,585,000 | 4/1986 | Hershenson et al. ............... 606/194 |
| 4,784,638 | 11/1988 | Ghajar et al. ..................... 604/264 |
| 4,801,297 | 1/1989 | Mueller ............................ 604/264 |
| 4,801,427 | 1/1989 | Jacob . |
| 4,818,488 | 4/1989 | Jacob . |
| 4,863,441 | 9/1989 | Lindsay et al. ................... 604/280 |
| 4,925,448 | 5/1990 | Bazaral . |
| 4,976,920 | 12/1990 | Jacob . |
| 5,021,044 | 6/1991 | Sharkawy ......................... 604/264 |
| 5,035,708 | 7/1991 | Alchas et al. . |
| 5,037,427 | 8/1991 | Harada et al. . |
| 5,200,158 | 4/1993 | Jacob . |
| 5,201,901 | 4/1993 | Harada et al. ..................... 623/1 |
| 5,344,402 | 9/1994 | Crocker . |
| 5,380,307 | 1/1995 | Chee et al. ....................... 604/264 |
| 5,397,355 | 3/1995 | Marin et al. . |
| 5,453,090 | 9/1995 | Martinez et al. ................... 606/108 |

Primary Examiner—Robert A. Hafer
Assistant Examiner—Justine R. Yu
Attorney, Agent, or Firm—Hoffmann & Baron, LLP

[57] ABSTRACT

A delivery system for transcutaneous insertion is capable of uniform gas sterilization. The delivery system includes a gas permeable elongated tubular catheter having an inner lumen and a gas permeable elongated tubular outer sheath axially surrounding the outer catheter. An implantable endoprosthesis is supported between the catheter and the outer sheath. The entire system including the catheter, sheath and endoprosthesis may be uniformly gas sterilized.

31 Claims, 5 Drawing Sheets

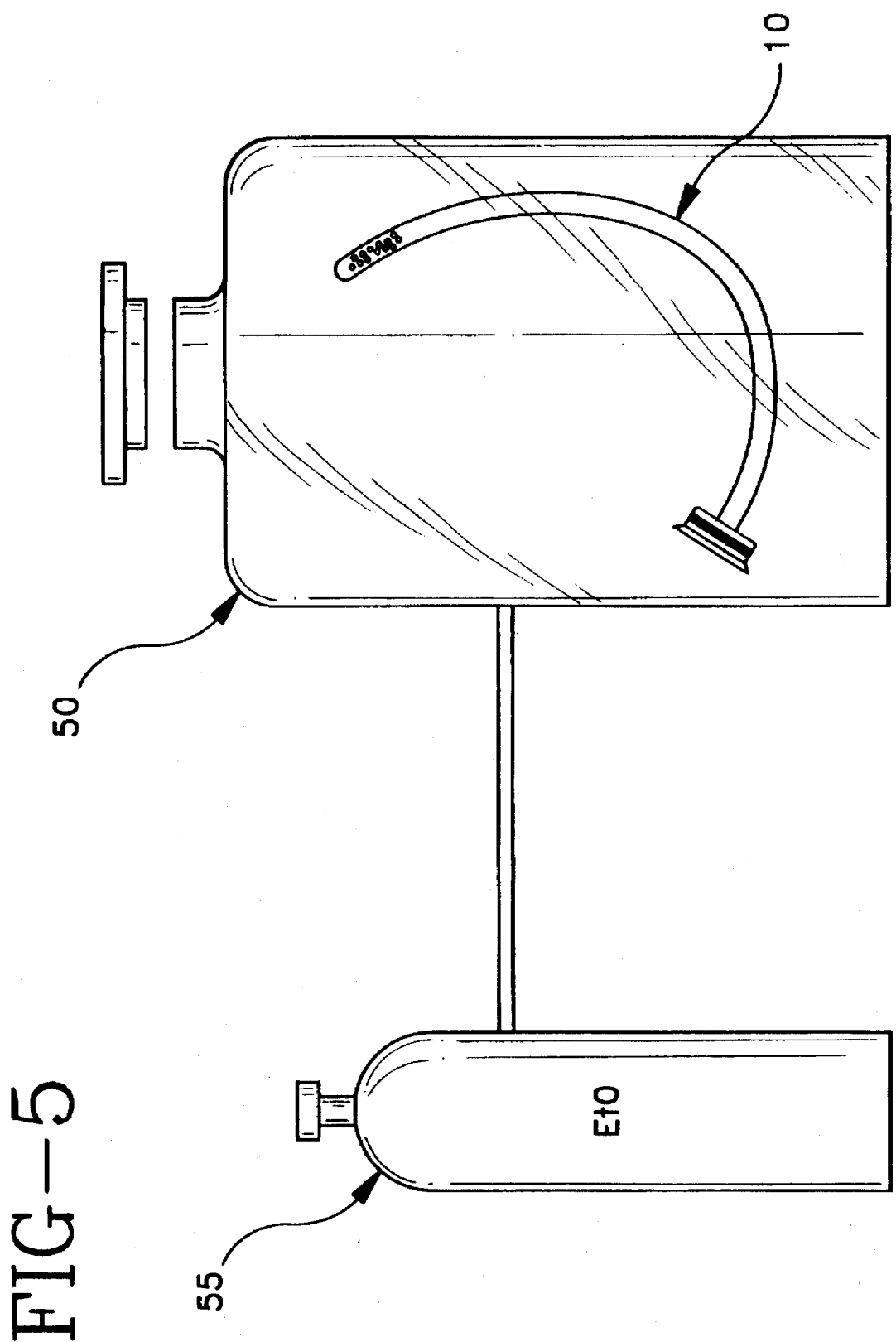

GAS STERILIZABLE INTRALUMINAL DELIVERY SYSTEM

FIELD OF THE INVENTION

The present invention relates generally to a delivery system for an implantable endoprosthesis that is capable of uniform gas sterilization. More particularly, the present invention relates to a delivery system for transcutaneous insertion capable of uniform gas sterilization which includes a gas permeable elongated tubular catheter having an inner lumen, a gas permeable elongated tubular outer sheath axially surrounding the catheter, and an implantable endoprosthesis supported between the catheter and the outer sheath.

BACKGROUND OF THE INVENTION

Modern medical practice requires the use of sterilized materials and instruments for surgical applications. Typically, the sterilization process occurs at the manufacturer of the material or instrument used, or at the hospital if the instrument is reusable.

It is well known in the art to sterilize instruments for medical use by way of gas sterilization. One major gas sterilization process in present use is that which employs ethylene oxide (EtO) gas. This process involves exposure of the medical device to EtO gas in the presence of a vacuum.

Commonly, surgical devices and instruments employed to deliver surgical devices are used in conjunction for surgical applications. For example, it is well known in the art to implant an endoprosthesis through transcutaneous insertion into the human body by way of catheter delivery. This procedure typically involves the insertion of a catheter intraluminally, followed by the insertion of the implantable endoprosthesis through the catheter to the area of implantation. Such procedures are commonly used particularly for implantation of vascular grafts.

The insertion of intraluminal catheters into a patient requires an absolutely sterile procedure since catheter contamination may cause life-threatening infections. However, it is common for the intraluminal implant device and the catheter to be packaged separately, and therefore sterilized separately. With separate sterilization, such devices may not be joined together until just prior to their use, i.e. in the operating room. This separate sterilization and later joining together of the components increases the possibilty of contamination and later infection.

Further, the transcutaneous insertion of an intraluminal implant device such as a graft requires that the implant device be inserted and contained within the lumen of the delivery catheter. In order to accomplish this containment, the graft is commonly compacted or folded. Attempts to sterilize a delivery system including a graft supported within a delivery catheter may be partially ineffective as it becomes difficult for the gas to effectively pass through the catheter as well as through the graft compacted within the catheter lumen. In such situations sterilization of the delivery system cannot be effectively achieved.

Accordingly, there is a need for a delivery system for an implantable intraluminal device that is capable of uniform sterilization of the entire delivery system including the mechanism for delivery and the implantable endoprosthesis itself.

SUMMARY OF THE INVENTION

It is an object of the present invention to provide a delivery system for transcutaneous insertion that is capable of uniform gas sterilization as an entire unit, including sterilization of the delivery mechanism, as well as effective sterilization of the endoprosthesis.

It is a further object of the present invention to provide an improved delivery system which includes a uniform gas sterilization delivery mechanism including a gas permeable elongated tubular catheter, a gas permeable elongated tubular outer sheath axially surrounding the catheter and an implantable endoprosthesis supported therebetween.

It is still a further object of the present invention to provide a delivery system for transcutaneous insertion capable of uniform gas sterilization including a gas permeable elongated tubular catheter with an inner lumen and longitudinally cylindrical shaped walls with an outer diameter and an inner diameter; a gas permeable elongated tubular outer sheath which axially surrounds the catheter and has longitudinally cylindrical shaped walls with an outer diameter and an inner diameter; and an implantable endoprosthesis supported between the catheter and the outer sheath, the endoprosthesis being transcutaneously deliverable within a tubular organ.

It is yet a further object of the present invention to provide a method of uniform gas sterilization of a catheter-endoprosthesis assembly.

In the efficient attainment of these and other objects, the present invention provides a delivery system consisting of a gas permeable elongated tubular catheter having an inner lumen, a gas permeable elongated tubular outer sheath axially surrounding the catheter, and an implantable endoprosthesis supported between the catheter and the outer sheath.

The implantable endoprosthesis is preferably a vascular graft for intravascular use. The vascular graft may include at least one stent for securing the vascular graft to a vascular surface. The stent may additionally contain stent barbs for engaging the vascular surface where the vascular graft is to be implanted.

The uniform gas sterilization is accomplished by the gas permeability of the outer sheath and the catheter. Preferably, the outer sheath and the catheter are made gas permeable by providing sheath openings in the sheath and catheter openings in the catheter. The sheath openings and the catheter openings are preferably located at an area adjacent the endoprosthesis. The sheath openings can be angled in a direction toward the distal end of the sheath. These angled sheath openings are particularly useful when the endoprosthesis is a graft secured by a stent with stent barbs. The angled sheath openings prevent the stent barbs from being insertably trapped within the sheath openings and therefore catching on the sheath. With the sheath openings angled toward the distal portion of the sheath, the barbs are free to move toward the distal end of the sheath.

The outer sheath may further contain sheath vent openings located at the proximal end of the outer sheath, to permit venting of gas from within the delivery system during gas sterilization. The catheter may also contain catheter vent openings located at the proximal portion of the catheter, to further permit venting of gas from within the delivery system during gas sterilization.

In its method aspect, the present invention provides a catheter-endoprosthesis assembly having a gas permeable elongated tubular catheter with an inner lumen, a gas permeable elongated tubular outer sheath axially surrounding the catheter, and an implantable endoprosthesis supported between the catheter and the outer sheath. This catheter-endoprosthesis assembly is exposed to sterilization gas permitting a flow of gas through the outer sheath, about the endoprosthesis, and through the catheter, thereby uniformly gas sterilizing the catheter-endoprosthesis system.

BRIEF DESCRIPTION OF THE DRAWINGS

FIG. 5 is a schematic view of a sterilization chamber used to sterilize the delivery system of the present invention.

DETAILED DESCRIPTION OF TEE PREFERRED EMBODIMENTS

Figure 1:
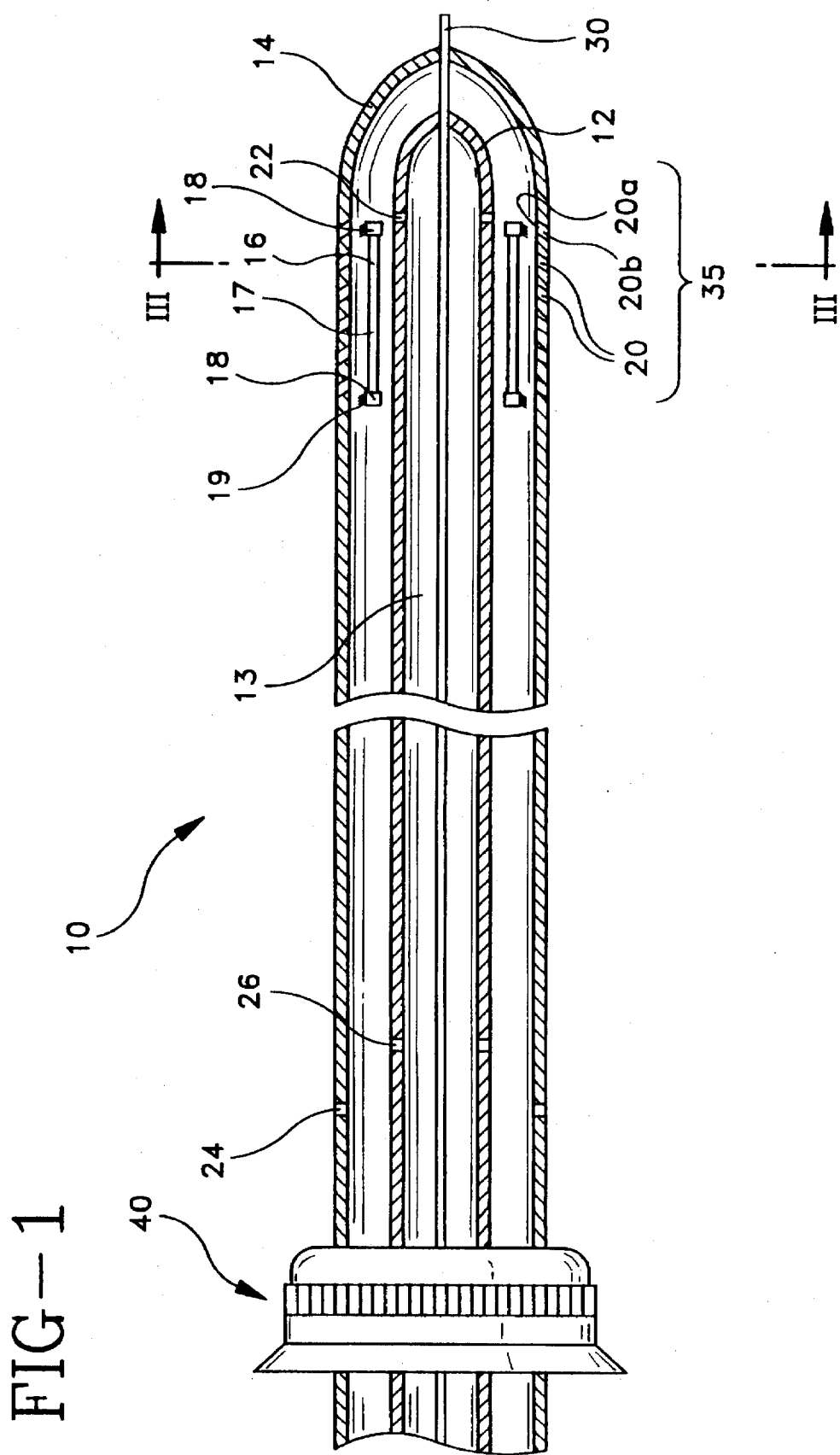
FIG. 1 is a longitudinal cross-sectional view of the delivery system of the present invention.

A delivery system for an implantable endoprosthesis capable of uniform gas sterilization as contemplated by the present invention is shown in FIG. 1. The delivery system 10 includes a catheter 12 having an inner lumen 13. Catheter 12 is an elongated tubular catheter that is common in the art of transcutaneous catheter delivery. Catheter 12 can be made of any generally flexible biocompatible material that is capable of transcutaneous insertion.

A gas permeable outer sheath 14 axially surrounds catheter 12. Outer sheath 14 may be also fabricated of any generally flexible bio-compatible material that is capable of transcutaneous insertion. Outer sheath 14 extends longitudinally generally the distance of catheter 12.

Figure 2:
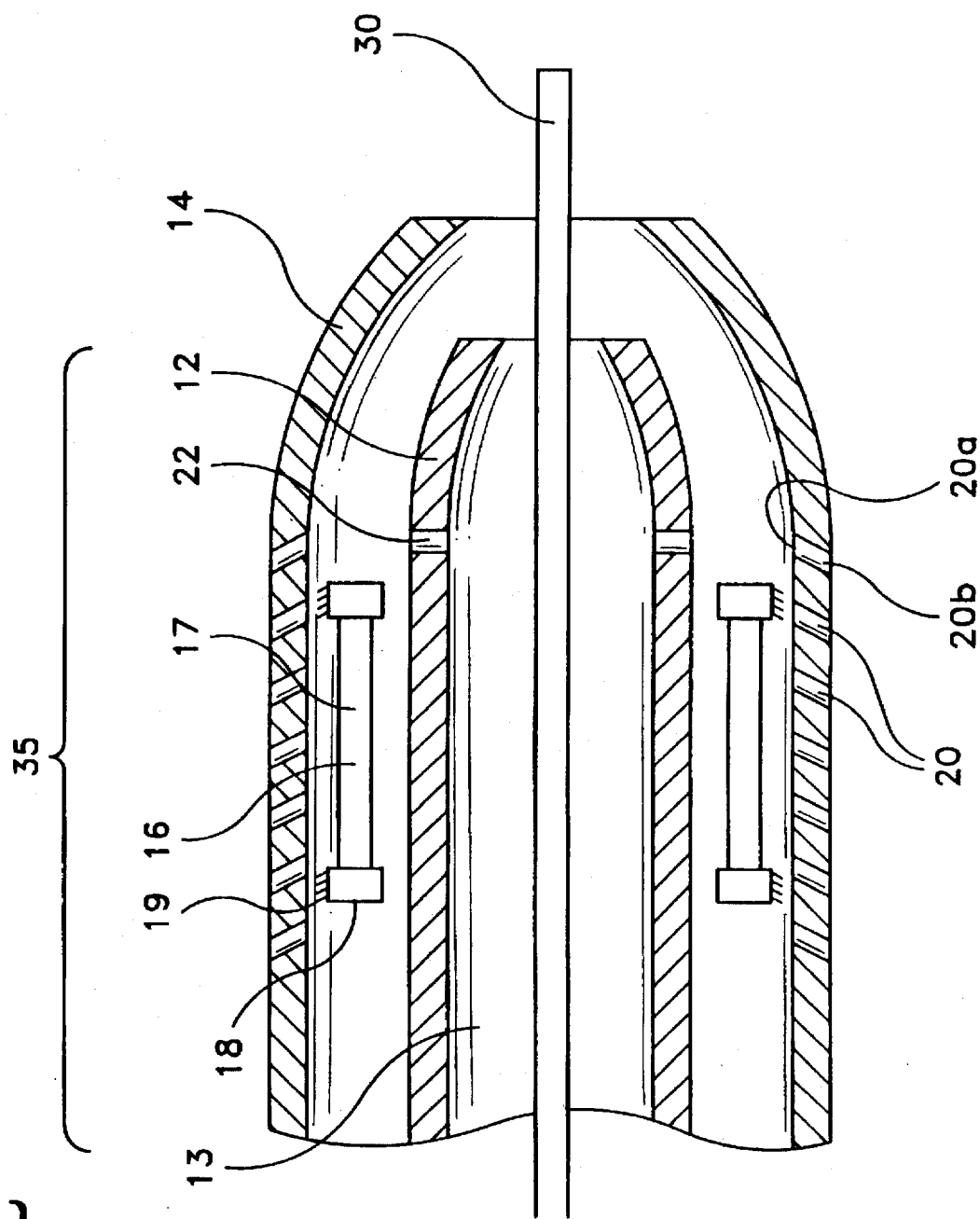
FIG. 2 is an enlarged longitudinal cross-sectional view of the delivery system of FIG. 1.
Figure 3:
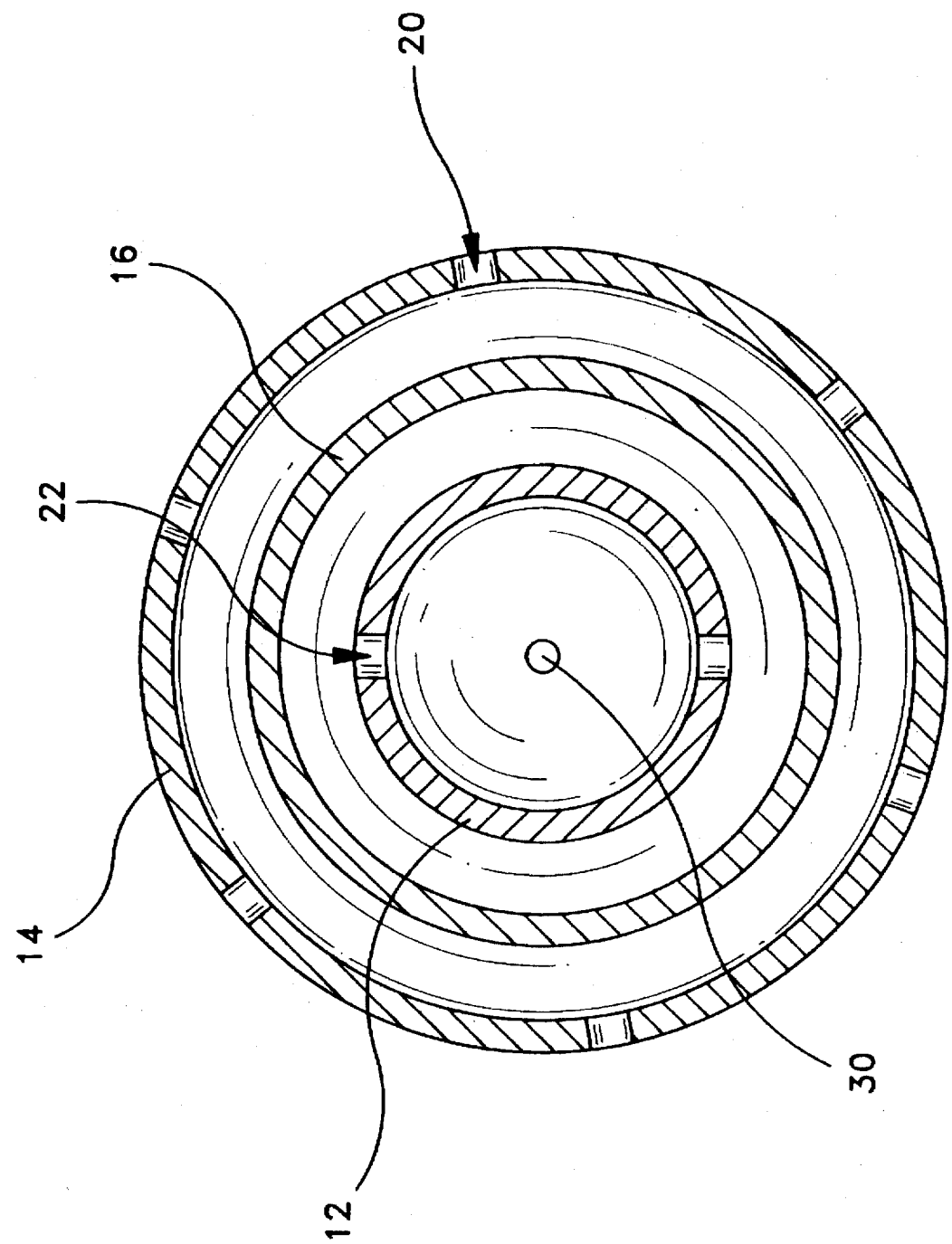
FIG. 3 is an enlarged vertical cross-sectional view of the delivery system of FIG. 1 taken along the lines III—III thereof.

As can be seen in FIGS. 1–3, implantable endoprosthesis 16 is supported between catheter 12 and outer sheath 14 generally at a location 35. Endoprosthesis 16 may be any type of implantable prosthetic device known in the art and which is implantable interluminally via a catheter. In preferred applications, endoprosthesis 16 may include a vascular graft 17 which may be constructed of braided, knitted, or woven synthetic yarns such as polyester or may be formed of an extruded plastic such as expanded polytetrafluoroethylene (PTFE). Graft 17 is designed for percutaneous implantation within a diseased or damaged blood vessel or other like vessel to provide replacement or reinforcement of the damaged vessel. Graft 17 may also be used to replace damaged or disease portions of blood vessels or similar fluid passageways.

Endoprosthesis 16 may further contain stent 18 for support. Stent 18 may be any conventional stent constructed of a variety of materials known in the art, such as stainless steel or other metals or alloys, polymeric materials or composites of polymers and metal. Stent 18 may be radially expandable between a first diameter and a second diameter different from the first diameter. Stent 18 may be self-expandable or may require other forces to enhance expansion. In the preferred embodiment shown herein, stent 18 is of the self-expanding type which is maintained in a compressed state by outer sheath 14.

To permit intraluminal delivery of endoprosthesis 16, graft 17 is folded or compressed. The compressed graft 17 along with stent 18 is supported in such compressed state between outer sheath 14 and catheter 12. Once properly deployed, the delivery system is appropriately removed and graft 17 opens in place assisted by the self-expansion of stents 18.

Further, stent 18 may contain stent barbs 19 which are outwardly extendable therefrom. These stent barbs 19 are commonly used in stent applications, aiding in positioning and anchoring of the supported endoprosthesis within the body lumen.

Figure 4:
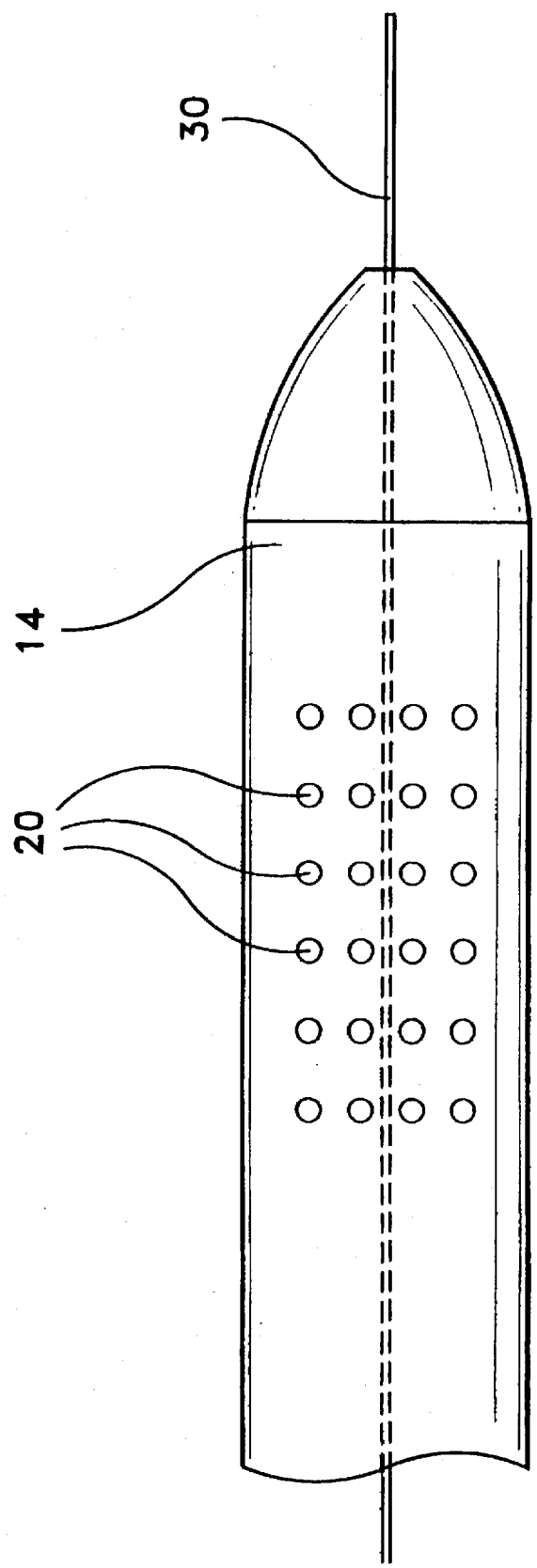
FIG. 4 is a plan view of an outer sheath of the delivery system of the present invention.

Outer sheath 14 may be made gas permeable by providing a plurality of sheath openings 20 depicted in FIG. 4. These sheath openings 20 are longitudinally spaced apart and extend through outer sheath 14. Sheath openings 20 are generally about 1 mm in diameter. Sheath openings 20 are preferably located in a position adjacent endoprosthesis 16 at location 35. Sheath openings 20 permit sterilizing gas to permeate through outer sheath 14, and sterilize both endoprosthesis 16 and delivery system 10.

Sheath openings 20 may be of any shape, but are preferably cylindrical or slitted. In preferred applications, sheath openings 20 are angled in a direction toward the distal portion of delivery system 10 such that the location of inner portion 20a of sheath openings 20 located on the inner surface of outer sheath 14 is in a position more distal of delivery system 10 than the location of outer portion 20b of sheath openings 20 on the outer surface of outer sheath 14. This angling of sheath openings 20 prevents stent barbs 19 from being insertibly trapped within sheath openings 20. Angling sheath openings 20 is particularly useful during the deployment of endoprosthesis 16 with stent 18 and stent barbs 19. Such deployment generally involves retracting outer sheath 14 while maintaining catheter 12 at the area of implantation. This retraction can cause stent barbs 19 to catch sheath openings 20 and prevent outer sheath 14 from retracting further. Angling sheath openings 20 avoids this problem by providing for free retraction of outer sheath 14.

Catheter 12 may be made gas permeable by providing a plurality of longitudinally spaced catheter openings 22. Catheter openings 22 extend through catheter 12 and are preferably located at a position adjacent endoprosthesis 16 at location 35. These catheter openings 22 permit sterilization gas to permeate through the catheter to further assure complete sterilization the delivery system 10.

Catheter 12 may have catheter vent openings 26. These catheter vent openings 26 extend through catheter 12 and are preferably located at a proximal portion of catheter 12 remote from location 19. Catheter openings 26 permit venting of said sterilization gas during gas sterilization.

Sheath 14 may have sheath vent openings 24, extending through sheath 14, preferably located at a proximal portion of sheath 14 remote from location 19. These sheath vent openings 24 function in a similar manner as catheter vent openings 26, permitting venting of sterilization gas.

The sheath 14 and catheter 12 of delivery system 10 are grouped together by connector 40. Connector 40 may be any type of connector known in the art of catheter delivery.

A guidewire 30 is slideably disposed within the inner lumen 13 of catheter 12. Guidewire 30 is extended out the distal end of catheter 12 and sheath 14 when employed within a body. Any type of guidewire generally known in the art may be employed.

In application, delivery system 10, including gas permeable catheter 12, gas permeable sheath 14, and implantable endoprosthesis 16 disposed therebetween, is inserted into a gas sterilization chamber 50 as depicted in FIG. 5.

Typically delivery system 10 is placed in an EtO compatible package and is preconditioned to increase the relative humidity inside of the package prior to the sterilization cycle. After the device is placed inside of chamber 50, chamber 50 is sealed, and a vacuum is established within chamber 50. Steam is then added to increase the chamber's relative humidity. After a set period of time, sterilization gas 55 is injected and the temperature and pressure inside of chamber 50 are increased. Sterilization gas 55 may be any type of gas used in the art for sterilization, but is preferably EtO gas. Sterilization gas levels are maintained at specific levels and durations known in the art for proper sterilization. After a set dwell time, chamber 50 is evacuated by reducing the pressure and pulling vacuum, using multiple cycles. Delivery system 10 is removed from chamber 50 and placed into an aeration room at increased temperature and air flow to produce a negative pressure within the room. Delivery system 10 remains in the aeration room for a set period, until the EtO residues are reduced to approved values.

During the sterilization process, outer sheath 14 permits the sterilization gas to permeate therethrough. The sterilization gas flows about and through endoprosthesis 16, notwithstanding the fact that graft 17 is compressed or folded between catheter 12 and outer sheath 14. Gas permeable catheter 12 also permits sterilization gas 55 to permeate therethrough to the inner lumen 13. This permeation of sterilization gas through the entire delivery system accounts for uniform sterilization and effective sterilization of the endoprosthesis 16 while it is maintained within delivery system 10.

In its preferred embodiment, outer sheath 14 is made gas permeable by sheath openings 20 adjacent endoprosthesis 16. Further, catheter 12 is made gas permeable by catheter openings 22 adjacent the vascular graft. The sheath openings 20 and catheter openings 22 permit permeation of sterilization gas 55 through the entire delivery system 10. Further, outer sheath 14 preferably contains sheath vent openings 24, while catheter 12 preferably contains catheter vent openings 26. These vent openings 24 and 26 permit sterilization gas 55 to exit from within delivery system 10 during the gas sterilization process, thereby creating a vented sterilization system.

As gas flow is more easily facilitated by the provision and location of openings 20 and 22 of sheath 14 and catheter 12 respectively, effective flow is provided through endoprosthesis 16. Such flow permits effective sterilization of graft 17 even in its compressed or folded state which is necessary in order to deliver graft 17 with delivery system 10.

The delivery system of the present invention may be utilized with any type of implantation procedure. In preferred applications, the delivery system of the present invention is utilized with transcutaneous insertion of an inplantable endoprosthesis. Most preferably, the delivery system of the present invention is utilized with percutaneous insertion of a stent supported vascular graft.

In this preferred application, a needle (not shown) is inserted percutaneously into a blood vessel (not shown). A guidewire 30 is then inserted through the needle and guided through the blood vessel to the area of implantation. The delivery system 10 including the catheter 12, the outer sheath 14 and the graft 17 with stent 18 and stent barbs 19 is then inserted into the blood vessel (not shown) and guided to the area of implantation over guidewire 30. Once at the point of implantation, outer sheath 14 is retracted by sliding outer sheath 14 in a longitudinal direction toward the proximate end of the delivery system 10. Such sliding movement allows the vascular graft 17 to unfold and exposes the vascular graft 17 to the vascular surface. Angled sheath openings 20 permit the outer sheath 14 to retract without engaging any of stent barbs 19 that are present to attach and anchor graft 17 to the vascular surface. After outer sheath 14 is removed and graft 17 is exposed, catheter 12 is removed by retracting catheter 12 in a longitudinal direction toward the proximal end of delivery system 10, away from graft 17, now implanted. As graft 17 with stent 18 was earlier supported and compressed between outer sheath 14 and catheter 12, but now graft 17 and stent 18 have no such support, stent 18 radially expands to its natural shape and stent barbs 19 anchor stent 18 and graft 17 into position on the vascular surface. Once stent 18 is expanded and anchored onto the vascular surface, catheter delivery system 10 and guidewire 30 can be removed from the blood vessel.

While the invention has been described herein in terms of certain preferred embodiments, those skilled in the art will recognize that various modifications can be made without departing from the scope of the present invention.

What is claim is:

1. A delivery system for transcutaneous insertion capable of uniform gas sterilization, said system comprising:
    a gas permeable elongated tubular catheter having an inner lumen;
    a gas permeable elongated tubular outer sheath axially surrounding said catheter, and
    an implantable endoprosthesis supported between said catheter and said sheath and extending for a given length of said sheath, said sheath including a plurality of sheath openings to permit permeation of sterilization was therethrough, said plurality of sheath openings extending along said given length of said sheath.

2. A delivery system of claim 1, wherein said endoprosthesis includes a vascular graft.

3. A delivery system of claim 2, wherein said endoprosthesis further includes at least one stent for securing said graft to a vascular surface.

4. A delivery system of claim 1, wherein said catheter includes catheter openings to permit permeation of said sterilization gas therethrough.

5. A delivery system of claim 4, wherein said catheter further includes catheter vent openings positioned at a second location remote from said first location of said supported graft, said catheter vent openings, permitting permeation of said sterilization gas therethrough.

6. A delivery system of claim 5, wherein said sheath further includes sheath vent openings positioned at a third location remote from said first location of said supported graft, said sheath vent openings permitting permeation of said sterilization gas therethrough.

7. A delivery system of claim 6, wherein said stent contains stent barbs which are outwardly extendable for engaging said vascular surface.

8. A delivery system of claim 7, wherein said sheath openings are angled toward the distal end of said sheath, preventing said stent barbs from being insertibly trapped within said sheath openings.

9. A method of uniform gas sterilization of a catheter-endoprosthesis assembly comprising the steps of:
    a. providing a catheter-endoprosthesis assembly including a gas permeable elongated tubular catheter having an inner lumen, a gas permeable elongated tubular outer sheath axially surrounding said catheter and including a plurality of sheath openings to permit permeation of sterilization gas therethrough, and an implantable endoprosthesis supported between said catheter and said sheath at a first location adjacent said sheath openings;
    b. exposing said catheter-endoprosthesis assembly to sterilization gas; and c. facilitating a flow of said gas through said sheath openings, around said endoprosthesis, and through said catheter, thereby uniformly gas sterilizing said catheter-endoprosthesis system.

10. A method of claim 9, wherein said providing step a. further includes providing said endoprosthesis including a vascular graft and at least one stent for securing said graft to a vascular surface.

11. A method of claim 10, wherein said providing step a further includes providing said catheter including catheter openings to permit permeation of said sterilization gas therethrough.

12. A method of claim 11, wherein said stent is provided with outwardly extendable stent barbs for engaging said vascular surface.

13. A method of claim 12, wherein said sheath is provided with sheath openings angled toward the distal end of said sheath, thereby preventing said stent barbs from being insertably trapped within said sheath openings.

14. In a delivery system having a catheter, an outer sheath, and an endoprosthesis supported therebetween, an improvement comprising:

a uniform gas sterilizable delivery mechanism whereby said catheter and said sheath are gas permeable, said endoprosthesis extending for a given length of said sheath and said sheath including sheath openings extending along said given length of said sheath.

15. A delivery system of claim 14, wherein said endoprosthesis includes a vascular graft.

16. A delivery system of claim 15, wherein said endoprosthesis further includes at least one stent for securing said graft to a vascular surface.

17. A delivery system of claim 16, wherein said catheter includes catheter openings to permit permeation of said sterilization gas therethrough.

18. A delivery system of claim 17, wherein said catheter further includes catheter vent openings positioned at a second location remote from said first location of said supported graft, said catheter vent openings permitting permeation of said sterilization gas therethrough.

19. A delivery system of claim 18, wherein said sheath further includes sheath vent openings positioned at a third location remote from said first location of said supported graft, said sheath vent openings permitting permeation of said sterilization gas therethrough.

20. A delivery system of claim 19, wherein said stent supporting said graft contains stent barbs which are outwardly extendable for engaging said vascular surface.

21. A delivery system of claim 20, wherein said sheath openings are angled toward the distal end of said sheath, thereby preventing said stent barbs from being insertably trapped within said sheath openings.

22. A delivery system for transcutaneous insertion of an endoprosthesis capable of uniform gas sterilization comprising:

a gas permeable elongated tubular catheter defining an inner lumen, said catheter having a longitudinal cylindrically shaped wall defining an outer diameter and an inner diameter;

a gas permeable elongated tubular outer sheath having a longitudinal cylindrically shaped wall defining an outer diameter and an inner diameter, said sheath axially surrounding said catheter; and an implantable endoprosthesis supported between said catheter and said sheath and extending for a given length of said sheath, said sheath including a plurality of longitudinally spaced sheath openings extending along said given length of said sheath and through said wall of said sheath between said outer diameter and said inner diameter, said endoprosthesis being transcutaneously deliverable within a tubular organ.

23. A delivery system of claim 22, wherein said endoprosthesis includes a vascular graft.

24. A delivery system of claim 23, wherein said endoprosthesis further includes at least one stent for securing said graft to a vascular surface.

25. A delivery system of claim 24, wherein said sheath openings are of a generally cylindrical shape.

26. A delivery system of claim 24, wherein said sheath openings are of a generally slitted shape.

27. A delivery system of claim 24, wherein said sheath further includes sheath vent openings positioned at a location remote from said supported graft, said sheath vent openings permitting permeation of sterilization gas therethrough.

28. A delivery system of claim 24, wherein said catheter includes a plurality of longitudinally spaced catheter openings, said catheter openings extending through said wall of said catheter between said outer diameter and said inner diameter.

29. A delivery system of claim 28, wherein said catheter further includes catheter vent openings positioned at a location remote from said supported graft, said catheter vent openings permitting permeation of said sterilization gas therethrough.

30. A delivery system of claim 24, wherein said stent supporting said graft contains stent barbs which are outwardly extendable for engaging said vascular surface.

31. A delivery system of claim 30, wherein said sheath openings extending through said sheath wall are angled such that the location of said sheath openings on said inner diameter of said sheath is more distal than the location of said sheath openings on said outer diameter of said sheath.

* * * * *

UNITED STATES PATENT AND TRADEMARK OFFICE
CERTIFICATE OF CORRECTION

PATENT NO. : 5,681,322
DATED : October 28, 1997
INVENTOR(S) : Hartigan, Jr.

It is certified that error appears in the above-indentified patent and that said Letters Patent is hereby corrected as shown below:

At column 6, lines 27-28, delete "permeation of sterilization was therethrough" and insert therefor --permeation of sterilization gas therethrough,--.

At column 7, line 17, delete "with sheath openings" and insert therefor --with said sheath openings--.

Signed and Sealed this

Twenty-fourth Day of March, 1998

Attest:

BRUCE LEHMAN

Attesting Officer

Commissioner of Patents and Trademarks